United States Patent
Piccardi

(10) Patent No.: US 10,022,315 B2
(45) Date of Patent: Jul. 17, 2018

(54) ORAL COMPOSITION FOR REINFORCING SKIN TOLERANCE FOLLOWING TOPICAL ADMINISTRATION OF A RETINOID COMPOUND

(71) Applicant: NUTRICOS TECHNOLOGIES, Clichy (FR)

(72) Inventor: Nathalie Piccardi, Arceau (FR)

(73) Assignee: LABORATOIRES INNEOV, Asnières (FR)

( * ) Notice: Subject to any disclaimer, the term of this patent is extended or adjusted under 35 U.S.C. 154(b) by 73 days.

(21) Appl. No.: 14/432,443

(22) PCT Filed: Sep. 27, 2013

(86) PCT No.: PCT/IB2013/058928
§ 371 (c)(1),
(2) Date: Mar. 30, 2015

(87) PCT Pub. No.: WO2014/049561
PCT Pub. Date: Apr. 3, 2014

(65) Prior Publication Data
US 2015/0258000 A1 Sep. 17, 2015

(30) Foreign Application Priority Data
Sep. 28, 2012 (FR) ..................................... 12 59213

(51) Int. Cl.
| | | |
|---|---|---|
| A61K 8/31 | (2006.01) | |
| A61K 8/368 | (2006.01) | |
| A61K 8/49 | (2006.01) | |
| A61Q 19/00 | (2006.01) | |
| A61K 8/97 | (2017.01) | |
| A61K 8/67 | (2006.01) | |
| A61K 8/36 | (2006.01) | |
| A61K 8/60 | (2006.01) | |

(52) U.S. Cl.
CPC .............. *A61K 8/676* (2013.01); *A61K 8/31* (2013.01); *A61K 8/361* (2013.01); *A61K 8/368* (2013.01); *A61K 8/49* (2013.01); *A61K 8/498* (2013.01); *A61K 8/602* (2013.01); *A61K 8/671* (2013.01); *A61K 8/97* (2013.01); *A61Q 19/00* (2013.01); *A61K 2800/75* (2013.01); *A61K 2800/88* (2013.01); *A61K 2800/92* (2013.01)

(58) Field of Classification Search
CPC ...... A61K 2800/92; A61K 8/31; A61K 8/361; A61K 8/368; A61K 8/49; A61K 8/498; A61K 8/602; A61K 8/671; A61K 8/676; A61K 8/97; A61Q 19/00
See application file for complete search history.

(56) References Cited

U.S. PATENT DOCUMENTS
| | | | |
|---|---|---|---|
| 5,516,793 A | 5/1996 | Duffy | |
| 5,703,122 A | 12/1997 | Duffy | |
| 2009/0076032 A1 | 3/2009 | Ward et al. | |

FOREIGN PATENT DOCUMENTS
| | | |
|---|---|---|
| CN | 1969800 A | 5/2007 |
| CN | 101766308 A | 7/2010 |
| CN | 101902927 A | 12/2010 |
| DE | 202004013660 U1 | 1/2005 |
| EP | 0858799 A2 | 8/1998 |
| EP | 1875894 A2 | 1/2008 |
| KR | 20070069625 A | 7/2007 |
| WO | 02/34210 A2 | 5/2002 |
| WO | 02/34233 A2 | 5/2002 |
| WO | 2009/050085 A1 | 4/2009 |
| WO | 2009/050101 A1 | 4/2009 |

OTHER PUBLICATIONS

Mukherjee et al., "Retinoids in the treatment of skin aging: an overview of clinical efficacy and safety," Clinical Interventions in Aging, 2006: 1(4) 327-348).*
Aug. 1, 2014 International Search Report issued in International Patent Application No. PCT/IB2013/058928.
Aug. 1, 2014 Written Opinion issued in International Patent Application No. PCT/IB2013/058928.
Jul. 30, 2013 Search Report issued in French Patent Application No. 1259213.
Jul. 30, 2013 Written Opinion issued in French Patent Application No. 1259213.
Dreno B; "Nouvelles Methods d'evaluation Appliquees a une Association Brevetee de Lacto-lycopene d'isoflavones de soja et de vitamine C dans la correction du vieillissement cutane;" Nouvelles Dermatologiques; Strasbourg, France; vol. 22, No. 8; Jan. 1, 2003; pp. 557-561; XP009068873.
Skovgaard et al.; "Effect of a novel dietary supplement on skin aging in post-menopausal women;" European Journal of Clinical Nutrition; vol. 60; Jan. 1, 2006; pp. 1201-1206; XP008080469.
Miao, "Make-Ups Make You Up: Perfect Care of Urban Women," Tianjin Science and Technology Press, First Edition, p. 220, Jan. 31, 2009.
Aug. 22, 2016 First Office Action issued in Chinese Application No. 201380062313.3.

* cited by examiner

*Primary Examiner* — Sreeni Padmanabhan
*Assistant Examiner* — Jody Karol
(74) *Attorney, Agent, or Firm* — Oliff PLC

(57) ABSTRACT

The cosmetic or non-therapeutic use of an oral composition for reinforcing an individual's skin tolerance to topical administration of a retinoid compound, the oral composition having at least one carotenoid, at least one phytoestrogen and vitamin C. A cosmetic or non-therapeutic process for increasing an individual's skin tolerance to topical administration of a retinoid compound, having at least one step of oral administration to the individual of an oral composition having at least one carotenoid, at least one phytoestrogen and vitamin C. A set for simultaneous, separate or sequential administration, the set having a first cosmetic composition for topical application having, in a physiologically acceptable medium, at least one effective amount of a retinoid compound, and a second composition for oral administration, for reinforcing the skin tolerance of the individual treated with the first composition, the second composition having at least one carotenoid, at least one phytoestrogen and vitamin C.

14 Claims, No Drawings

ORAL COMPOSITION FOR REINFORCING SKIN TOLERANCE FOLLOWING TOPICAL ADMINISTRATION OF A RETINOID COMPOUND

The present invention aims to provide a novel use of an oral composition for the purpose of increasing the skin tolerance of a subject with regard to a topical cosmetic treatment with at least one retinoid compound.

In the context of the present invention, the cosmetic treatments considered are more particularly those dedicated to acting on the skin.

The term "skin" is intended to mean the whole of the skin of the human body, including the areas of the skin covered with body hair. Thus, in particular, the skin of the face, of the neckline, of the arms and of the legs, the lips and the scalp are targeted.

Human skin consists of three compartments, namely a superficial compartment, which is the epidermis, the dermis and a deep compartment, which is the hypodermis. The epidermis is a keratinized, stratified pavement epithelium. It is mainly constituted, i.e. 90% constituted, of keratinocytes, but also of other cells, and rests on a basal membrane which separates it from the dermis.

The dermis is a connective tissue. Its architecture results from the arrangement and the interactions between the constituents of the extracellular matrix and the fibroblasts, which carry out the synthesis thereof and the degradation thereof. The dermis makes up the main bulk of the skin. It is constituted of collagen fibers and elastic fibers, and also of glycosaminoglycans (GAGs) and proteoglycans. These different structures form a complex network which plays a key role in the biomechanical properties of the skin.

Unfortunately, the set of properties of the skin is not unaffected.

First of all, the skin is continually exposed to physical, chemical, mechanical or infectious external attacks, produced in particular by the climate, ultraviolet radiation, tobacco, pollution and/or xenobiotics, for instance microorganisms.

Finally, it is irreparably subject to chronobiological aging and to photoinduced aging or dermatoheliosis. These aging phenomena manifest themselves through a set of characteristic clinical signs which are seated on skin that is chronically exposed to light: uneven pigmentation, pigmentary spots, dull and yellow complexion, laxity, wrinkles, dryness, roughness, etc.

Histologically, the predominant modifications in the dermis are in particular represented by elastosis, a mass constituted of dystrophic elastic fibers.

From a biochemical point of view, there is a disruption of the metabolic activity of fibroblasts, associated with qualitatively and quantitatively abnormal syntheses of the extracellular matrix components, elastin, collagen and glycosaminoglycans.

From a pathogenic point of view, while the deleterious role of ultraviolet radiation and in particular ultraviolet A radiation in the creation of photoinduced aging is now well demonstrated, the molecular mechanisms involved remain poorly understood. Oxidative stress caused by ultraviolet irradiation probably plays a key role in the formation of dermal damage, in the modification of the genetic program of fibroblasts and in the activation of matrix metalloproteases, which are enzymes that participate in extracellular matrix degradation.

Moreover, at the menopause, skin aging accelerates and the thickness of the dermis and of the epidermis decreases. Furthermore, it is known that the hormonal deficiencies associated with the menopause are accompanied by a general slowing of cell metabolism. Women then experience a sensation of "dry skin" or taut skin, and an accentuation of the surface wrinkles and fine lines is observed. The skin has a rough aspect on palpation. Finally, the skin exhibits reduced suppleness.

All the phenomena described above lead to the appearance of signs of skin aging. The expression "signs of skin aging" is intended to mean all the modifications of the external appearance of the skin due to aging, whether chronobiological and/or photoinduced or associated with the menopause, such as, for example, wrinkles and fine lines, withered skin, flaccid skin, thinned skin, dull skin that lacks radiance, a lack of elasticity and/or of tonicity of the skin.

For obvious reasons, all of these modifications or signs of skin aging are often difficult for the individual to accept, generally for esthetic reasons.

Retinoids or retinoid compounds remain the reference topical medical treatment for skin aging, whether it is chronobiological or photoinduced, reducing in particular deep wrinkles and fine lines, laxity of the skin and hyperpigmentation However, as for any topical product, the effects of retinoids on the signs of skin aging are only truly effective after 6 months of treatment and most treatments go well beyond 6 months. As it happens, these active agents are not without adverse side effects which limit their skin tolerance by patients.

There is therefore a need for products capable of reinforcing an individual's skin tolerance with regard to a topical cosmetic treatment with at least one retinoid compound, capable of producing adverse effects (in particular tautness, redness, desquamation, a burning sensation and a feeling of discomfort as set out hereinafter), and more particularly skin ailments.

There is still a need for cosmetic products and processes capable of providing a subject, topically treated in parallel with a retinoid compound, capable of producing adverse side effects and more particularly skin ailments, with a feeling of comfort.

The object of the present invention is to satisfy these needs.

According to a first of its aspects, the present invention relates to the cosmetic or non-therapeutic use of an oral composition for reinforcing an individual's skin tolerance to topical administration of a retinoid compound, said oral composition comprising at least one carotenoid, at least one phytoestrogen and vitamin C.

Preferentially, said at least one carotenoid is lycopene.

Preferentially, said at least one phytoestrogen is an isoflavonoid.

The topical administration of a retinoid compound can be intended for combating all the signs of skin aging, namely chronobiological aging or photoinduced aging or alternatively skin aging associated with the menopause.

Thus, the present invention also relates to the cosmetic or non-therapeutic use of an oral composition comprising at least one carotenoid, at least one phytoestrogen and vitamin C, for improving skin tolerance to skin ailments which may be caused by the topical administration of at least one retinoid compound, in particular for combating skin aging.

For the purposes of the invention, the expression "reinforcing skin tolerance" means reducing or even preventing the manifestation of adverse side effects on the skin or adverse skin ailments produced by the topical administration of the retinoid active agent.

For the purposes of the present invention, the skin ailment under consideration, which appears reactionally upon application of the retinoid compound to the skin, can more particularly take the form of redness and/or pruritus. The skin ailment can also manifest itself through dryness or desquamation of the skin. Finally, the skin ailment can take the form of hot, heating or burning sensations and/or tingling sensations, itching sensations or even feelings of tautness. All of these skin ailments can also be grouped together under the general term of skin irritation or alternatively of skin discomfort reactions.

Thus, the inventors have noted, surprisingly and unexpectedly, that the administration of an oral composition in accordance with the invention makes it possible to significantly increase the skin tolerance threshold of a subject who is simultaneously receiving topical cosmetic treatment using at least one retinoid compound having a potential irritable nature. The reduction of the adverse effects caused by these treatments, obtained through the administration of the oral composition in accordance with the present invention, enables better adherence to said treatments by the subjects treated.

Admittedly, food supplements related to the oral compositions considered according to the invention have already been provided, and in particular in application WO 02/34210, for cosmetic use. However, these supplements are essentially put forward therein for their stimulatory effect on collagen synthesis and/or their inhibitory effect on collagenases. Given this biological activity, it is proposed to use them in cosmetic compositions dedicated to preventing and/or treating the signs of skin aging, it being possible for these compositions to optionally also contain other active agents, in particular anti-inflammatories, keratolytic agents, free-radical scavengers, or else agents which modulate the differentiation and/or proliferation and/or pigmentation of the skin, like, for example, retinoic acid and vitamin D, and derivatives thereof.

Consequently, to the knowledge of the inventors, the effectiveness of such oral compositions for reducing or even preventing an intolerance reaction induced by a related cosmetic treatment has never been characterized, and the use of these oral compositions for these purposes has been described even less so.

As it happens, as emerges from the tests presented hereinafter, it is noted that the administration of an oral composition in accordance with the invention makes it possible to obtain significant reinforcement of the skin tolerance threshold of a subject jointly subjected to a topical treatment using a retinoid compound capable of producing or presumed to produce adverse effects. It has in particular been shown that the oral administration of a composition as defined above makes it possible to reduce the general discomfort created by anti-skin-aging treatment via topical administration of a retinoid compound. What is more, this gain in skin tolerance is in no way obtained to the detriment of the effectiveness of the cosmetic treatment, which remains confirmed, or even improved.

According to another of its aspects, the present invention relates to a cosmetic or non-therapeutic process for increasing an individual's skin tolerance to topical administration of a retinoid compound, comprising at least one step of oral administration to said individual of an oral composition comprising at least one carotenoid, at least one phytoestrogen and vitamin C.

According to one particular embodiment of this aspect, the process is characterized in that the topical administration and the oral administration are carried out at least partly together.

According to another particular embodiment of this aspect, the process is characterized in that said topical administration and said oral administration are carried out simultaneously, separately or sequentially.

According to another of its aspects, the invention relates to a set for simultaneous, separate or sequential administration, said set comprising a first cosmetic composition for topical application comprising, in a physiologically acceptable medium, at least one effective amount of a retinoid compound, and a second composition for oral administration, for reinforcing the skin tolerance of the individual treated with the first composition, said second composition comprising at least one carotenoid, at least one phytoestrogen, preferably an isoflavonoid, and vitamin C.

Retinoid Compound

Among the retinoid compounds, mention may be made of retinol and esters thereof, retinal, retinoic acid and derivatives thereof such as those described in documents FR-A-2 570 377, EP-A-199 636, EP A-325 540 and EP-A-402 072, and adapalene.

Among the retinoid compounds most commonly used in the treatment of skin aging, mention may in particular be made of retinoic acid, tretinoin, isotretinoin, retinol, retinaldehyde, adapalene, tazarotene and alitretinoin. Retinyl acetate, retinyl propionate, retinyl palmitate and seletinoid G can also be cited insofar as studies have been carried out on these retinoid derivatives, which offer potentials in the field of the treatment of skin aging.

Salts and derivatives, for instance cis or trans forms, racemic mixtures, and dextrorotatory or levorotatory forms of the compounds mentioned above are also included in the definition for the purposes of the present invention of "retinoid compound".

The retinoid compound may be present in a topical composition used in the context of the invention, in particular in the set or kit which is also the subject of the invention, in a content ranging from 0.001% to 0.15% by weight, preferably from 0.005% to 0.1% by weight and better still from 0.01% to 0.05% by weight, relative to the total weight of the topical composition.

Carotenoid

In the context of present invention the term "carotenoid" is intended to mean both a carotenoid with provitamin A activity and a carotenoid with no provitamin A activity.

Needless to say, according to the invention, the carotenoid may be a mixture of carotenoids with provitamin A activity and of carotenoids with no provitamin A activity. This mixture may be in any proportion.

According to the invention, the carotenoid with provitamin A activity may be a mixture of carotenoids with provitamin A activity. This mixture may be in any proportion. Among the carotenoids with provitamin A activity, examples that may be mentioned include β-carotene or α-carotene, preferably β-carotene.

According to the invention, the carotenoid with no provitamin A activity may be a mixture of carotenoids with no provitamin A activity. This mixture may be in any proportion. Among the carotenoids with no provitamin A activity, examples that may be mentioned include zeaxanthin, cryptoxanthin, lutein or lycopene.

More particularly, said at least one carotenoid used in the context of the present invention is lycopene.

Astaxanthin is also a carotenoid which may be suitable for the invention.

The carotenoid used according to the invention may be of natural or synthetic origin. The term "natural origin" is intended to mean the carotenoid in pure form or in solution irrespective of its concentration in said solution, obtained from a natural element, such as a plant extract. For example, when the carotenoid is lycopene, a tomato extract may more particularly be used.

The term "synthetic origin" is intended to mean lycopene in pure form or in solution irrespective of its concentration in said solution, obtained via chemical synthesis. The lycopene which may be used in the context of the present invention maybe in cis or trans chemical form.

When the carotenoid is of natural origin, it may be obtained from plant material derived from the whole plant cultivated in vivo or derived from in vitro culture.

The term "cultivated in vivo" is intended to mean any cultivation of standard type, i.e. in soil in the open air or in a greenhouse, or alternatively out of the soil.

The term "in vitro culture" is intended to mean all the techniques known to those skilled in the art for artificially obtaining a plant or a plant part. The selection pressure imposed by the physicochemical conditions during the growth of plant cells in vitro makes it possible to obtain a standardized plant material that is available throughout the year, in contrast with plants cultivated in vivo.

Preferentially, according to the invention, a plant derived from in vivo culture is used. Any extraction method known to those skilled in the art may be used to prepare the carotenoid used according to the invention.

Very preferentially in the case of lycopene, a lycopene-rich tomato extract is used.

Lycopene is also present in melon, guava and grapefruit.

The lycopene may be in alcoholic solution, in particular ethanolic solution. The carotenoid may also be in lipidic or lipoalcoholic solution.

By way of example, according to the invention, a lycopene-rich tomato extract, prepared by the company Lycored, sold under the name LycOMato®, consisting of an oleoresin extract containing, for example, from 6 to 10% of pure lycopene, can be used.

The lycopene may be in an aqueous suspension. For this, it is possible to use forms that are water-dispersible, under cold or hot conditions, as sold by the company Lycored under the name Lyc-o-Mato CWD.

Any other more complex lycopene-based ingredient may also be used for implementing the invention.

Thus, a "more complex ingredient" is intended to mean, for example, a primary composition comprising lycopene and a whey protein. This primary composition is in particular described in document WO 01/91588. This primary composition is also known as lactolycopene. It is this ingredient which is used in the food supplement of example 1. It has the advantage of increasing the bioavailability of the lycopene and/or of being easy to formulate in food supplements (sachet, gel capsule, tablet, sugar-coated tablet, soft capsule, etc, forms).

The lactolycopene may in particular be sold by the company Indena.

The amount of extract that may be used according to the invention obviously depends on the desired effect, and may thus vary within a wide range.

To give an order of magnitude, the lycopene may be used in pure form in an amount representing from 0.0001% to 50% by weight, preferably from 0.001% to 10% by weight, preferentially in an amount representing from 0.02% to 5% by weight relative to the total weight of the oral composition in accordance with the present invention.

Needless to say, if those skilled in the art use the carotenoid, in particular lycopene, in the form of a solution or a plant extract, for example, they know how to adjust the amount of solution that they use in their composition in order for the final amount of carotenoid in the composition to be in accordance with the predefined usable amounts.

Phytoestrogen

Phytoestrogens are a family of non-steroidal compounds naturally produced by plants, which encompasses isoflavones, and also the phytoestrogens contained in hops, or lignans, in particular those of flax and of Schizandra chinensis.

Isoflavones are natural substances (heterocyclic phenols) belonging to the flavonoid family. In soybean grains, the concentrations of isoflavones (daidzein and genistein) or glycosylated forms thereof (daidzine, genistine) are high. By virtue of their structural similarity to female hormones of estrogen type, genistein and daidzein are also known as phytoestrogens or phytohormones. In contrast with flavonoids, they are present in only a limited number of plants: soybean (milk, grain, meal) is the main source.

Isoflavonoids

Isoflavonoids constitute a subclass of flavonoids, formed from a 3-phenylchroman backbone which may comprise varied substituents and different oxidation levels. In contrast with flavonoids, they are present in only a very limited number of plants.

Isoflavonoids encompass several classes of compounds, among which mention may be made of isoflavones, isoflavanones, rotenoids, pterocarpans, isoflavanes, isoflavan-3-enes, 3-arylcoumarins, 3-aryl-4-hydroxycoumarins, coumestanes, coumaronochromones, α-methyldeoxybenzoins or 2-arylbenzofurans.

For a complete review of isoflavonoids, their analysis methods and their sources, those skilled in the art may advantageously refer to chapter 5 "Isoflavonoids" written by P. M. Dewick in The Flavonoids, published by Harbone, pp. 125-157 (1988).

The isoflavonoids that are suitable for use in the present invention may be of natural or synthetic origin. The term "natural origin" is intended to mean an isoflavonoid in pure form or in solution at various concentrations, obtained via various extraction processes from an element, generally a plant, of natural origin. The term "synthetic origin" is intended to mean an isoflavonoid in pure form or in solution at various concentrations, obtained via chemical synthesis.

It is preferred to use isoflavonoids of natural origin. Among these, mention may be made of: daidzein, formononetin, cuneatin, genistein, isoprunetin and prunetin, cajanine, orobol, pratensein, santal, junipegenin A, glycitein, afrormosin, retusin, tectorigenin, irisolidone, jamaicine, and also analogs and/or metabolites thereof.

According to the present invention, among the isoflavonoids, it is preferred to use isoflavones, including the glycosylated forms and the aglycone forms. Among the isoflavones, the simplest isoflavones are preferred, among which are daidzein, daidzine, genistein, genistine, equol and mixtures thereof Daidzine, daidzein, genistine and genistein are present in particular in the soybean extract (*Glycina max*) available from Archer Daniels Midland Company under the name Novasoy®.

Processes for preparing isoflavones are in particular described in WO 95/10530, WO 95/10512, U.S. Pat. Nos. 5,679,806, 5,554,519, EP-812 837 and WO 97/26269.

In one composition in accordance with the invention, the isoflavonoids are preferentially chosen from isoflavones, isoflavanones, rotenoids, pterocarpans, isoflavanes, isoflavan-3-enes, 3-arylcoumarins, 3-aryl-4-hydroxycoumarins, coumestanes, coumaronochromones, α-methyldeoxybenzoins and 2-arylbenzofurans.

In particular, the isoflavonoids may be chosen from daidzein, formononetin, cuneatin, genistein, isoprunetin and prunetin, cajanine, orobol, pratensein, santal, junipegenin A, glycitein, afrormosin, retusin, tectorigenin, irisolidone, jamaicine, and also analogs and/or metabolites thereof.

In addition, an isoflavonoid that is suitable for use in the invention may be chosen from genistine, daidzine, genistein, daidzein, glycitine, equol, formononetin, cuneatin, isoprunetin and prunetin, cajanine, orobol, pratensein, santal, junipegenin A, glycitein, afrormosin, retusin, tectorigenin, irisolidone, jamaicine, and also analogs and/or metabolites thereof.

In certain embodiments, said isoflavonoid is an isoflavone, or a mixture of isoflavones.

In certain embodiments, said isoflavonoid is chosen from daidzine, daidzein, genistine and genistein, or a mixture thereof.

In certain embodiments, said isoflavonoid is chosen from daidzein and genistein, or a mixture thereof.

In certain embodiments, said at least one isoflavone is in the form of a mixture of isoflavones.

In certain embodiments, said at least one isoflavone is in the form of an extract of soybean isoflavones.

By way of illustration, an extract of soybean isoflavones may be, for example, the extract of soybean (*Glycina max*) available from Archer Daniels Midland Company under the name Novasoy®.

Such soybean isoflavones may also be used in the composition in accordance with the invention in the form of a soybean extract, which in particular may be sold by the company ADM.

The lycopene and the soybean extract may also be used in a composition in accordance with the invention within a single ingredient, in particular sold by the company Indena under the name Lycosypremix.

To give an order of magnitude, the soybean isoflavones may be used in an amount representing from 0.001% to 50% by weight, preferably from 0.01% to 30% by weight, preferentially in an amount representing from 1% to 15% by weight relative to the total weight of the oral composition in accordance with the present invention.

Vitamin C

According to the invention, the vitamin C or ascorbic acid and/or analogs thereof may be used alone or as mixtures of any nature and any proportion and may be of natural or synthetic origin.

Ascorbic acid is generally in L form, since it is particularly found in this form in the plant world.

The amount of vitamin C that may be used according to the invention obviously depends on the desired effect, and may thus vary within a wide range.

The vitamin C which may be used in the oral composition in accordance with the present invention may in particular be the one sold by the company DSM.

To give an order of magnitude, in the composition of the invention, the vitamin C in pure form may be present in a content ranging from 0.0001% to 50% by weight, preferably from 0.1% to 30% by weight, and preferentially in a content ranging from 0.2% to 15% by weight relative to the total weight of the composition.

Of course, if the vitamin C is present in the form of a solution, for example a plant extract, those skilled in the art will know how to adjust the amount of this solution in the composition according to the invention so as to obtain the vitamin C concentration ranges described above.

Additional Active Agent

An oral composition in accordance with the invention may advantageously also comprise an additional, in particular cosmetic, dermatological or pharmaceutical, active agent.

Advantageously, such an additional cosmetic, dermatological or pharmaceutical active agent may be intended to exert a cosmetic, care or hygiene effect on the skin.

An additional active agent is advantageously chosen by those skilled in the art in such a way that it does not harm the effect of the active agent of the invention. In particular, an additional active agent that is suitable for the invention can be chosen from active agents intended to reinforce the skin barrier.

According to another embodiment, it is possible to combine, with an active agent of the invention, active agents intended for the prevention and/or treatment of skin affections.

By way of additional active agents that can be used according to the invention, mention may be made of:
- vitamins, such as vitamin A, B5, B6, B8, D, E or PP (vitamin B3 or niacin),
- antioxidants, such as curcuminoids, polyphenol compounds, flavonoids such as catechins; proanthocyanidins, anthocyanins, OPCs (oligomeric proanthocyanidins); ubiquinones, coffee extracts containing polyphenols and/or diterpenes; chicory extracts; ginkgo biloba extracts; proanthocyanidin-rich grape extracts; capsicum extracts,
- minerals, such as zinc, calcium, magnesium, copper, iron, iodine, manganese, selenium and chromium (III),
- sugars,
- amino acids, in particular sulfur-comprising amino acids such as glutathione precursors, taurine and selenium amino acids,
- 3 and 6 polyunsaturated fatty acids,
- prebiotics, chosen in particular from oligosaccharides, produced from glucose, galactose, xylose, maltose, sucrose, lactose, starch, xylan, hemicellulose, inulin, gums of acacia type, for example, or a mixture thereof. More particularly, the oligosaccharide comprises at least one fructooligosaccharide. More particularly, this prebiotic may comprise a mixture of fructooligosaccharide and of inulin,
- phytosterols,
- le resveratrol,
- hesperidin,
- or mixtures thereof.

As additional active agents in an oral galenical formula, any commonly used and/or permitted ingredients may also be considered. By way of illustration, mention may be made of vitamins, minerals, essential lipids, trace elements, polyphenols, flavonoids, antioxidants such as lipoic acid and coenzyme Q10, prebiotics, proteins and amino acids, monosaccharides and polysaccharides, amino sugars, phytosterols and triterpenic alcohols of plant origin.

This may in particular involve vitamins A, D, E and PP and the group B vitamins, in particular B5, B6 and B8.

The minerals and trace elements particularly used are zinc, calcium, magnesium, copper, iron, iodine, manganese, selenium and chromium (III).

Among the polyphenols, polyphenols from grape, from tea, from olive, from cocoa, from coffee, from apple, from blueberry, from elderberry, from strawberry, from cranberry and from onion may also in particular be selected.

Preferably, among the amino acids suitable for the invention, taurine, threonine, cysteine, tryptophan or methionine, or peptides and proteins containing them, may be chosen.

Preferably, among the lipids suitable for the invention, lipids belonging to the group of oils containing monounsaturated and polyunsaturated fatty acids, such as oleic acid, linoleic acid, alpha-linolenic acid, gamma-linolenic acid, stearidonic acid, long-chain fish omega-3 fatty acids such as EPA and DHA, and conjugated fatty acids derived from plants or animals, such as CLAs (conjugated linoleic acids), may be chosen.

Thus, a composition intended for oral administration may also comprise at least one nutritional active agent chosen from vitamin E and polyphenol compounds.

An oral composition of the invention may also comprise other nutritional active agents chosen from:
  anti-aging nutritional active agents, such as food antioxidants, nutrients with free-radical-scavenging properties and cofactors of endogenous antioxidant enzymes, vitamins A and E, xanthophylls, certain minerals such as zinc, copper, magnesium or selenium, lipoic acid, coenzyme Q10, superoxide dismutase (SOD) or taurine. Among the anti-aging active agents, mention may be made in particular of the unsaponifiable fractions extracted from lipids of plant origin, Aloe vera, native or hydrolyzed marine collagen, and plant or marine oils rich in omega-3 and omega-6 fatty acids (including gamma-linolenic acid),
  photoprotective nutritional active agents, such as antioxidants and free-radical scavengers, vitamins A and E, xanthophylls, certain minerals such as zinc, copper, magnesium and selenium, coenzyme Q10 and superoxide dismutase (SOD),
  nutritional ingredients with moisturizing or immunomodulating properties, such as an extract of *Polypodium leucotomos*, and plant or marine oils rich in omega-3 and omega-6 fatty acids, including gamma-linolenic acid.

According to another embodiment, a depurative agent, in particular chosen, for example, from birch extracts or black radish extracts, may also be present in the oral composition in accordance with the invention.

Set or Kit

Alternatively, the oral composition under consideration according to the invention can be used in a set for simultaneous, separate or sequential administration.

Such a set can be packaged in separate packages, and can in particular be packaged in one and the same package.

Such a set may comprise a first cosmetic composition for topical administration comprising, in a physiologically acceptable medium, at least one effective amount of a retinoid compound, and a second composition for oral administration, for reinforcing the skin tolerance of the individual treated with the first composition, said second composition comprising at least one carotenoid, at least one phytoestrogen and vitamin C.

Use and Process

The oral administration of the composition in accordance with the invention can be carried out prior to, together with and/or subsequent to the topical application of a retinoid compound, for which it is sought to dispense with the adverse skin reactions that it is capable of inducing.

In some embodiments of the cosmetic use or process of the invention, said topical administration and said oral administration are carried out at least partly together.

In some embodiments of the cosmetic use or process of the invention, said topical administration and said oral administration of the composition in accordance with the invention are carried out simultaneously, intermittently, or separately over time.

For the purposes of the invention, said topical administration of the retinoid compound and said oral administration of the compound in accordance with the invention are carried out simultaneously when the implementation of the process comprises at least one period of time during which the topical administration of the retinoid compound and the oral administration of the composition in accordance with the invention are applied/administered simultaneously, i.e. during the same 24 hour period, for example during the same day, where appropriate at distinct moments of the same 24 hour period, where appropriate of the same day. Said period of time during which the topical administration of the retinoid compound and the oral composition are applied/administered simultaneously may be of variable duration.

For the purposes of the invention, said topical administration of the retinoid compound and the oral administration of the composition in accordance with the invention are carried out intermittently when the topical administration of the retinoid compound and the oral administration of the composition in accordance with the invention are administered alternately over time, i.e. at intervals of more than 24 hours. When the topical administration and the oral administration are carried out intermittently (i) the period of topical administration, between the beginning and the end of said administration, and (ii) the period of oral administration, between the beginning and the end of said oral treatment, overlap.

For the purposes of the invention, said topical application and said oral administration are carried out separately over time when said topical composition comprising at least one retinoid compound and said oral composition in accordance with the invention are administered during periods of time which never overlap.

Thus, the composition for oral administration above can be successfully used to partially or totally reduce the residual skin ailments resulting from the topical treatment using a retinoid compound, when said composition for oral administration is administered subsequent to said cosmetic treatment. In other words, said composition for oral administration can be successfully used in particular subsequent to treatment with the retinoid compound.

Alternatively, it may be advantageous for the beginning of the topical treatment using a retinoid compound to be preceded by a preliminary period of administration of the oral composition in accordance with the present invention.

According to one advantageous embodiment of the invention, the cosmetic process is characterized in that it comprises:
  the oral administration, during a first period of time, of said oral composition in accordance with the invention,
  the administration, during a second period of time, of a topical administration of at least one retinoid compound;
it being understood that at least one part of said first period of time and at least one part of said second period of time are simultaneous.

The fact that at least one part of said first period of time and at least one part of said second period of time are simultaneous defines a joint period of administration of the two compositions.

The oral administration can in this case be performed at least once per period of time. Preferably, the periods of time may be broken into units of time, in particular of equal duration, for example into days or weeks. Typically, a cosmetic use or process according to the invention may be performed on a daily basis for example, at a rate of, for example, a single administration per day or one administration twice a day, for example once in the morning and once in the evening.

Thus, according to one embodiment, the process of the invention comprises (i) a first period of time comprising the administration of the oral composition in accordance with the invention, in the absence of topical administration of the retinoid compound, said first period of time being followed (ii) by a second period of time comprising the simultaneous or intermittent administration of the oral composition in accordance with the invention and of the retinoid compound topically.

According to another embodiment, the process of the invention comprises one and the same period of time comprising the simultaneous or intermittent administration of the oral composition in accordance with the invention and of the retinoid composition topically.

Thus, in some embodiments of the process, said oral cosmetic composition is administered during only a part or during the whole of the duration of administration of the retinoid compound topically.

As already stated previously, a topical treatment with retinoic acid can last a few months, in particular between three months and a year, in particular approximately 6 months.

The retinoid compound can thus be topically administered continuously, i.e. daily, or intermittently, for a period ranging from 10 days to 360 days, in particular from 30 days to 240 days, and from 60 days to 180 days, for example 60 days.

Advantageously, the composition in accordance with the invention can be orally administered continuously, i.e. daily, or intermittently, for a period ranging from 10 days to 360 days, in particular from 30 days to 240 days, and from 60 days to 180 days, for example 60 days.

According to one particular embodiment, the process according to the invention is intended for menopausal women.

Oral Composition

The expression "cosmetic composition for oral administration" or "oral cosmetic composition" is intended to mean, for example, nutritional, nutraceutical or cosmeceutical compositions comprising at least one carotenoid, at least phytoestrogen and vitamin C.

An oral composition in accordance with the invention comprises a physiologically, nutritionally or dermatologically acceptable medium.

According to one particular embodiment, the oral composition is suitable for the daily administration of a combination of compounds comprising (i) from 1 to 25 mg of carotenoid, (ii) from 10 to 300 mg of phytoestrogen and (iii) from 10 to 1000 mg of vitamin C.

In the case of compositions that are suitable for oral administration, the use of an ingestible support is preferred. The ingestible support may be of diverse nature according to the type of composition under consideration.

For ingestion, numerous embodiments of oral compositions and in particular of food supplements are possible.

Such compositions may be formulated via any common process known to those skilled in the art.

Thus, a composition in accordance with the invention may preferably take the form of a sugar-coated tablet, a gel capsule, a suspension, a gel, an emulsion, an oral solution, a tablet to be swallowed or chewed, a capsule, in particular a soft or hard capsule, a granule to be dissolved, a syrup, a lozenge or a food supplement.

In particular, an oral composition in accordance with the invention may take any of the forms of food supplements or enriched foods, for example food bars or compacted or loose powders. The powders may be diluted with water, in soda, dairy products or soybean derivatives, or may be incorporated into food bars.

According to one preferred embodiment, a composition in accordance with the invention administered orally may be formulated in the form of sugar-coated tablets, gel capsules, gels, emulsions, tablets, capsules, hydrogels, food bars, compact or loose powders, liquid suspensions or solutions, confectionery products, fermented milks, fermented cheeses, chewing gum, toothpaste or spray solutions.

Milk, yogurt, cheese, fermented milks, milk-based fermented products, ice creams, fermented or nonfermented cereal-based products, milk-based powders, infant and baby formulae, animal feed in particular for pets, tablets or lozenges, liquid bacterial suspensions, oral supplements in dry form and oral supplements in liquid form are, for example, suitable as food supports.

The oral compositions may be either in anhydrous form or in aqueous form.

An oral composition in accordance with the invention may be formulated with the usual excipients and components for such oral compositions or food supplements, i.e. in particular fatty and/or aqueous components, humectants, thickeners, preserving agents, texture agents, taste agents and/or coating agents, antioxidants, preserving agents and dyes that are common in the food sector.

The formulating agents and excipients for oral compositions, and in particular for food supplements, are known in this field and are not the subject of a detailed description herein.

In particular, a composition in accordance with the invention may be a food composition for human consumption. This may be, in particular, nutritional complete foods, drinks, mineral waters, soups, dietary supplements and replacement or substitute foods, nutrional bars, confectionery, milk-based products or fermented milk-based products, yogurts, milk-based powders, enteral nutritional products, infant and/or baby compositions, fermented or nonfermented cereal-based products, ice creams, chocolate, coffee, "culinary" products such as mayonnaise, tomato puree or salad dressings.

The examples that follow illustrate the invention without limiting the scope thereof.

EXAMPLES

Example 1

Formula for Food Supplement in the Form of a Tablet

The dosage is 2 tablets/day.

| Ingredient | Supplier | Unit composition (mg/tablet) |
|---|---|---|
| ACTIVE INGREDIENTS | | |
| 2% Lactolycopene (1) | Indena | 150.00 |
| Soybean extract (2) | ADM | 62.50 |
| Vitamin C (3) | DSM | 43.33 |
| EXCIPIENTS | | |
| Dibasic calcium phosphate dihydrate | Univar/JRS | 245.80 |
| Silicified microcrystalline cellulose 2% | JRS | 163.87 |
| Sodium Croscarmellose | JRS | 21.00 |
| Silicon dioxide | Keyser & Mackay | 7.20 |
| Colloidal silicon dioxide | Degussa | 3.50 |
| Magnesium stearate | Quimdis | 2.80 |
| Opadry white | Colorcon | 14.00 |
| Opadry pink | Colorcon | 21.42 |

(1) Equivalent to 3 mg of lycopene/tablet
(2) Equivalent to 25 mg of isoflavones/tablet
(3) Equivalent to 30 mg of vitamin C/tablet

Example 2

Formula for Food Supplement in the Form of a Tablet

The dosage is 2 tablets/day.

| Ingredient | Supplier | Unit composition (mg/tablet) |
|---|---|---|
| ACTIVE INGREDIENTS | | |
| Lycosoypremix (1% lycopene) (1) | Indena | 210.530 |
| Vitamin C (2) | DSM | 28.890 |
| EXCIPIENTS | | |
| Dibasic calcium phosphate dihydrate | Univar | 76.790 |
| Microcrystalline cellulose | SPCI | 76.790 |
| Colloidal silicon dioxide | Degussa | 6.000 |
| Sodium croscarmellose | JRS | 4.000 |
| Magnesium stearate | Quimdis | 1.000 |
| FILM-COATING AGENTS | | |
| Shellac | Emiga | 5.000 |
| Talc | Dousselin | 61.220 |
| Sucrose | Unipex | 264.153 |
| Titanium dioxide | Lambert Rivière | 0.510 |
| Carnauba wax | Unipex | 0.140 |

(1) Equivalent to 2 mg de lycopene/tablet and to 16.67 mg of isoflavones/tablet
(2) Equivalent to 20 mg of vitamin C/tablet

Example 3

Clinical Study

The beneficial effect, in terms of reinforcing skin tolerance, of the food supplement of example 1 was assessed in a clinical study carried out according to the protocol which follows:

The study performed under dermatological control (30 dermatologists) was carried out in menopausal women (n=203), from 50 to 66 years old and showing moderate signs of photo-aging on the face.

These women were divided up into two treatment groups:

- group 1 treated with 0.05% by weight retinoic acid, relative to the total weight of the composition, for 6 months at a rate of one application per day (control group),
- group 2 treated with 0.05% by weight retinoic acid, relative to the total weight of the composition, for 6 months at a rate of one application per day, combined with daily intake of the food supplement as described in example 1.

3.1 Evaluation of Symptoms

The symptoms associated with skin tolerance were evaluated after 60, 120 and 180 days by, on the one hand, dermatologists and, on the other hand, by the subjects themselves.

Dermatologist Scoring Scale

| | | mild | | | moderate | | | Substantial | | |
|---|---|---|---|---|---|---|---|---|---|---|
| On the face | Zero | + | ++ | +++ | + | ++ | +++ | + | ++ | +++ |
| Signs of skin dryness | 0 | 1 | 2 | 3 | 4 | 5 | 6 | 7 | 8 | 9 |
| Signs of desquamation | 0 | 1 | 2 | 3 | 4 | 5 | 6 | 7 | 8 | 9 |
| Signs of redness | 0 | 1 | 2 | 3 | 4 | 5 | 6 | 7 | 8 | 9 |
| Pruritus | 0 | 1 | 2 | 3 | 4 | 5 | 6 | 7 | 8 | 9 |
| Hot sensations | 0 | 1 | 2 | 3 | 4 | 5 | 6 | 7 | 8 | 9 |

TABLE 1

Evaluation of the signs on the skin associated with the side effects of retinoic acid by the dermatologists (*$p < 0.05$). The results are expressed in terms of mean scores.

| | | GROUP 1 | GROUP 2 |
|---|---|---|---|
| Sign of skin dryness | D0 | 3.2 | 3 |
| | D60 | 2.7 | 2.4 |
| | D120 | 2.2 | 1.6* |
| | D180 | 1.7 | 1.1* |
| Sign of desquamation | D0 | 1.6 | 1.6 |
| | D60 | 1.8 | 1.5 |
| | D120 | 1.5 | 1.1 |
| | D180 | 1.1 | 0.7 |
| Sign of redness | D0 | 1.2 | 1.2 |
| | D60 | 1.6 | 1.3 |
| | D120 | 1.3 | 0.8* |
| | D180 | 1.0 | 0.6* |
| Pruritus | D0 | 0.6 | 0.5 |
| | D60 | 1.2 | 1.1 |
| | D120 | 0.9 | 0.6* |
| | D180 | 0.6 | 0.4* |

Throughout the study, the dermatologists observed fewer signs of intolerance to the treatment in group 2 compared with group 1. The food supplement tested therefore makes it possible to limit, in a statistically significant manner, the side effects of the topical application of retinoic acid.

Patient Scoring Scale

During the last 2 months, have you experienced on the face

| | None | Mild | Moderate | Severe |
|---|---|---|---|---|
| feelings of discomfort | None | Mild | Moderate | Severe |
| tautness | None | Mild | Moderate | Severe |
| itching | None | Mild | Moderate | Severe |
| desquamation | None | Mild | Moderate | Severe |
| redness | None | Mild | Moderate | Severe |

TABLE 2

Evaluation of the signs on the skin associated with the side effects of retinoic acid by the patients ($*p < 0.05$).

| | | GROUP 1 | GROUP 2 |
|---|---|---|---|
| Signs of discomfort | D60 | 43% (N), 42% (Mi), 15% (Mo), 0% (S) | 48% (N), 46% (Mi), 5% (Mo), 2% (S) |
| | D120* | 52% (N), 35% (Mi), 13% (Mo), 0% (S) | 68% (N), 29% (Mi), 3% (Mo), 0% (S) |
| | D180* | 62% (N), 31% (Mi), 7% (Mo), 0% (S) | 75% (N), 23% (Mi), 2% (Mo), 0% (S) |
| Tautness | D60 | 40% (N), 49% (Mi), 10% (Mo), 1% (S) | 51%, 41%, 7%, 1% |
| | D120 | 49% (N), 43% (Mi), 8% (Mo), 0% (S) | 63% (N), 32% (Mi), 5% (Mo), 0% (S) |
| | D180* | 57% (N), 35% (Mi), 7% (Mo), 1% (S) | 74% (N), 23% (Mi), 3% (Mo), 0% (S) |
| Itching | J60* | 37% (N), 48% (Mi), 15% (Mo), 0% (S) | 52% (N), 47% (Mi), 7% (Mo), 1% (S) |
| | D120* | 51% (N), 42% (Mi), 7% (Mo), 0% (S) | 71% (N), 26% (Mi), 3% (Mo), 0% (S) |
| | D180* | 61% (N), 35% (Mi), 4% (Mo), 0% (S) | 75% (N), 22% (Mi), 3% (Mo), 0% (S) |
| Desquamation | D60* | 37% (N), 41% (Mi), 21% (Mo), 1% (S) | 48% (N), 43% (Mi), 9% (Mo), 1% (S) |
| | D120* | 44% (N), 42% (Mi), 14% (Mo), 0% (S) | 60% (N), 31% (Mi), 8% (Mo), 1% (S) |
| | D180* | 57% (N), 35% (Mi), 8% (Mo), 0% (S) | 71% (N), 26% (Mi), 3% (Mo), 0% (S) |
| Redness | D60 | 41% (N), 46% (Mi), 13% (Mo), 0% (S) | 53% (N), 39% (Mi), 8% (Mo), 0% (S) |
| | D120* | 43% (N), 49% (Mi), 7% (Mo), 1% (S) | 68% (N), 29% (Mi), 3% (Mo), 0% (S) |
| | D180* | 59% (N), 35% (Mi), 6% (Mo), 0% (S) | 73% (N), 26% (Mi), 1% (Mo), 0% (S) |

(N): none;
(Mi): mild;
(Mo): moderate;
(S): severe

Throughout the study, the subjects felt fewer signs of skin discomfort in group 2 compared with group 1. The food supplement tested therefore makes it possible to statistically reduce the feelings of skin discomfort relating to the topical application of retinoic acid.

3.2 Overall Evaluation of Tolerance

Skin tolerance to the treatments was checked after 60, 120 and 180 days by means of questionnaires given to the dermatologists and the subjects participating in the study.

Tables 1 (evaluations by the dermatologists) and 2 (self-evaluation by the subjects) summarize the skin tolerance results obtained in groups 1 and 2. The results are expressed as of subjects, in reply to the following question: "do you consider thus far that the tolerance to the treatment is". The possible replies were excellent, good, average and poor.

TABLE 3

Evaluation by the dermatologists of the skin tolerance to the treatments in groups 1 and 2

| | GROUP 1 | | | GROUP 2 | | |
|---|---|---|---|---|---|---|
| | D60 | D120 | D180 | D60 | D120 | D180 |
| Excellent | 15% | 20% | 23% | 34% | 47% | 53% |
| Good | 62% | 58% | 63% | 56% | 49% | 44% |
| Average | 24% | 23% | 15% | 10% | 5% | 3% |
| Poor | 0% | 0% | 0% | 0% | 0% | 0% |
| G1 vs G2 | Statistically significant difference from D60 onward in favor of G2 ($p < 0.001$) | | | | | |

TABLE 4

Evaluation by the subjects of the skin tolerance to the treatments in groups 1 and 2

| | GROUP 1 | | | GROUP 2 | | |
|---|---|---|---|---|---|---|
| | D60 | D120 | D180 | D60 | D120 | D180 |
| Excellent | 18% | 25% | 30% | 31% | 40% | 51% |
| Good | 63% | 54% | 53% | 55% | 54% | 43% |
| Average | 20% | 21% | 15% | 13% | 6% | 6% |
| Poor | 0% | 1% | 2% | 1% | 0% | 0% |
| G1 vs G2 | Statistically significant difference from D60 onward in favor of G2 ($p < 0.05$) | | | | | |

By way of illustration of the skin tolerance at D180, with regard to the various symptoms set out hereinafter, the subjects gave the self-evaluations as reported in table 5 hereinafter:

The symptoms selected for these evaluations are:
decrease in redness,
decrease in desquamation,
decrease in itching,
decrease in tautness, and
decrease in skin discomfort.

TABLE 5

Evaluation of the symptoms by the subjects, at D180

| | GROUP 1 D180 | GROUP 2 D180 |
|---|---|---|
| Redness | 59% (N), 35% (Mi), 6% (Mo), 0% (S) | 73% (N), 26% (Mi), 1% (Mo), 0% (S) |
| Desquamation | 57% (N), 35% (Mi), 8% (Mo), 0% (S) | 71% (N), 26% (Mi), 3% (Mo), 0% (S) |
| Itching | 61% (N), 35% (Mi), 4% (Mo), 0% (S) | 75% (N), 22% (Mi), 3% (Mo), 0% (S) |
| Tautness | 57% (N), 35% (Mi), 7% (Mo), 1% (S) | 74% (N), 23% (Mi), 3% (Mo), 0% (S) |
| Feeling of skin discomfort | 62% (N), 31% (Mi), 7% (Mo), 0% (S) | 75% (N), 23% (Mi), 2% (Mo), 0% (S) |

(N): None;
(Mi): mild presence;
(Mo): moderate presence;
(S): severe presence

The differences are significant at $p<0.01$ for "redness", "desquamation", "itching" and "feeling of skin discomfort" and at $p<0.05$ for "tautness".

These tests clearly demonstrated the effectiveness of the administration of an oral composition according to the invention for reinforcing an individual's skin tolerance to topical administration of a retinoid compound.

The invention claimed is:
1. A cosmetic or non-therapeutic method for reinforcing an individual's skin tolerance to topical administration of a retinoid compound, comprising at least:
- a step of topical administration of a retinoid compound to the individual for combating chronobiological aging or photoinduced aging or skin aging associated with menopause, and
- a step of oral administration of a composition comprising at least one carotenoid, at least one phytoestrogen and vitamin C to the individual for increasing the individual's skin tolerance to the topical administration of the retinoid compound,
- wherein the composition is suitable for the daily administration of a combination of compounds comprising (i) from 1 to 25 mg of carotenoid, (ii) from 10 to 300 mg of phytoestrogen, and (iii) from 10 to 1000 mg of vitamin C, and
- said individual being a menopausal woman.

2. The method as claimed in claim 1, wherein the retinoid compound is chosen from retinoic acid, tretinoin, isotretinoin, retinol, retinaldehyde, adapalene, tazarotene and alitretinoin.

3. The method as claimed in claim 1, for improving skin tolerance to skin ailments which may be caused by the topical administration of at least one retinoid compound.

4. The method as claimed in claim 3, wherein the skin ailments manifest themselves through redness, pruritus, dryness or desquamation of the skin, hot, heating or burning sensations and/or tingling sensations, itching sensations or even feelings of tautness.

5. The method as claimed in claim 1, wherein said at least one carotenoid is lycopene.

6. The method as claimed in claim 1, wherein said at least one phytoestrogen is an isoflavonoid.

7. The method as claimed in claim 1, wherein the isoflavonoid is chosen from genistine, daidzine, genistein, daidzein, glycitine, equol, formononetin, cuneatin, isoprunetin and prunetin, cajanine, orobol, pratensein, santal, junipegenin A, glycitein, afrormosin, retusin, tectorigenin, irisolidone, jamaicine, and also analogs and/or metabolites thereof- or a mixture thereof.

8. The method as claimed in claim 6, wherein the isoflavonoid is an isoflavone.

9. The method as claimed in claim 1, wherein the topical administration and the oral administration are carried out together.

10. The method as claimed in claim 1, wherein the topical administration and the oral administration are carried out simultaneously, intermittently or sequentially.

11. The method as claimed in claim 1, wherein it comprises (i) a first period of time comprising the administration of the oral composition as defined in claim 1, in the absence of topical administration of the retinoid compound, said first period of time being followed (ii) by a second period of time comprising the simultaneous or intermittent administration of said oral composition and of the retinoid compound topically.

12. The method as claimed in claim 1, wherein it comprises one and the same period of time comprising the simultaneous or intermittent administration of the oral composition as defined in claim 1 and of the retinoid compound topically.

13. The method as claimed in claim 8, wherein the isoflavonoid is in the form of an extract of soybean isoflavones.

14. The method as claimed in claim 6, wherein the isoflavonoid is selected from the group consisting of isoflavones, isoflavanones, rotenoids, pterocarpans, isoflavanes, isoflavan-3-enes, 3-arylcoumarins, 3-aryl-4-hydroxycoumarins, coumestanes, coumaronochromones, α-methyldeoxybenzoins and 2-arylbenzofurans.

* * * * *